United States Patent
Sun et al.

(10) Patent No.: US 9,012,702 B2
(45) Date of Patent: Apr. 21, 2015

(54) CATALYTIC DEHYDROCHLORINATION OF HYDROCHLOROFLUOROCARBONS

(75) Inventors: Xuehui Sun, Swedesboro, NJ (US); Mario Joseph Nappa, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 13/370,337

(22) Filed: Feb. 10, 2012

(65) Prior Publication Data

US 2012/0215037 A1     Aug. 23, 2012

Related U.S. Application Data

(60) Provisional application No. 61/444,879, filed on Feb. 21, 2011.

(51) Int. Cl.
*C07C 17/25* (2006.01)
*C07C 21/18* (2006.01)

(52) U.S. Cl.
CPC ........................... *C07C 17/25* (2013.01)

(58) Field of Classification Search
CPC ........................................... C07C 17/25
USPC .................. 570/156, 155, 157, 227, 226
See application file for complete search history.

(56) References Cited

U.S. PATENT DOCUMENTS

| | | | |
|---|---|---|---|
| 4,978,649 A | 12/1990 | Suroviklin et al. | |
| 5,136,113 A | 8/1992 | Rao | |
| 7,829,748 B1 * | 11/2010 | Tung et al. | 570/164 |
| 8,530,708 B2 * | 9/2013 | Wang et al. | 570/156 |
| 2007/0197842 A1 * | 8/2007 | Mukhopadhyay et al. | 570/155 |
| 2009/0043136 A1 * | 2/2009 | Wang et al. | 570/136 |
| 2009/0043137 A1 | 2/2009 | Wang et al. | |
| 2009/0299107 A1 | 12/2009 | Wang et al. | |
| 2012/0215035 A1 | 8/2012 | Nappa et al. | |
| 2012/0215036 A1 | 8/2012 | Sun et al. | |
| 2012/0215038 A1 | 8/2012 | Sun et al. | |

FOREIGN PATENT DOCUMENTS

| | | |
|---|---|---|
| CN | 101772480 A | 7/2010 |
| EP | 2135855 A3 | 3/2010 |
| WO | 2009021154 A2 | 2/2009 |

OTHER PUBLICATIONS

Chinese Office Action and Search Report dated May 28, 2014, issued in Chinese Patent Application No. 201280009802.8 (in Chinese and in English).

Mexican Office Action dated Oct. 21, 2014, issued in Mexican Patent Application No. MX/a/2013-009580.

* cited by examiner

*Primary Examiner* — Jafar Parsa
*Assistant Examiner* — Medhanit Bahta
(74) *Attorney, Agent, or Firm* — Scully, Scott, Murphy & Presser, P.C.

(57) ABSTRACT

A dehydrochlorination process is disclosed. The process involves contacting $R_fCFClCH_2X$ with a catalyst in a reaction zone to produce a product mixture comprising $R_fCF{=}CHX$, wherein said catalyst comprises MY supported on carbon, and wherein $R_f$ is a perfluorinated alkyl group, X =H, F, Cl, Br or I, M=K, Na or Cs, and Y=F, Cl or Br.

13 Claims, 2 Drawing Sheets

CATALYTIC DEHYDROCHLORINATION OF HYDROCHLOROFLUOROCARBONS

BACKGROUND

1. Field of the Disclosure

This disclosure relates in general to the catalytic dehydrochlorination of hydrochlorofluorocarbons to make hydrofluoroolefins. More specifically, the catalysts are alkali metal compounds supported on carbon.

2. Description of Related Art

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. The new HFC refrigerants, HFC-134a ($CF_3CH_2F$) being the most widely used at this time, have zero ozone depletion potential and thus are not affected by the current regulatory phase-out as a result of the Montreal Protocol.

In addition to ozone depleting concerns, global warming is another environmental concern. Thus, there is a need for heat transfer compositions that have not only low ozone depletion potentials, but also low global warming potentials. Certain hydrofluoroolefins (HFOs) meet both goals. Thus there is a need for making hydrofluoroolefins that have lower global warming potential than current commercial refrigeration products. HFO-1234yf ($CF_3CF=CH_2$) is one such hydrofluoroolefin.

Hydrofluoroolefins can find applications not only as refrigerants, but also as solvents, foam expansion agents, cleaning agents, aerosol propellants, dielectrics, fire extinguishants and power cycle working fluids. For example, HCFO-1224yd ($CF_3CF=CHCl$) can be used as a foam expansion agent, fire extinguishant, refrigerant, et al.

BRIEF SUMMARY OF THE DISCLOSURE

The present disclosure provides a dehydrochlorination process. The process comprises contacting $R_fCFClCH_2X$ with a catalyst in a reaction zone to produce a product mixture comprising $R_fCF=CHX$, wherein said catalyst comprises MY supported on carbon, and wherein $R_f$ is a perfluorinated alkyl group, X=H, F, Cl, Br or I, M=K, Na or Cs, and Y=F, Cl or Br.

DETAILED DESCRIPTION

Figure 1:
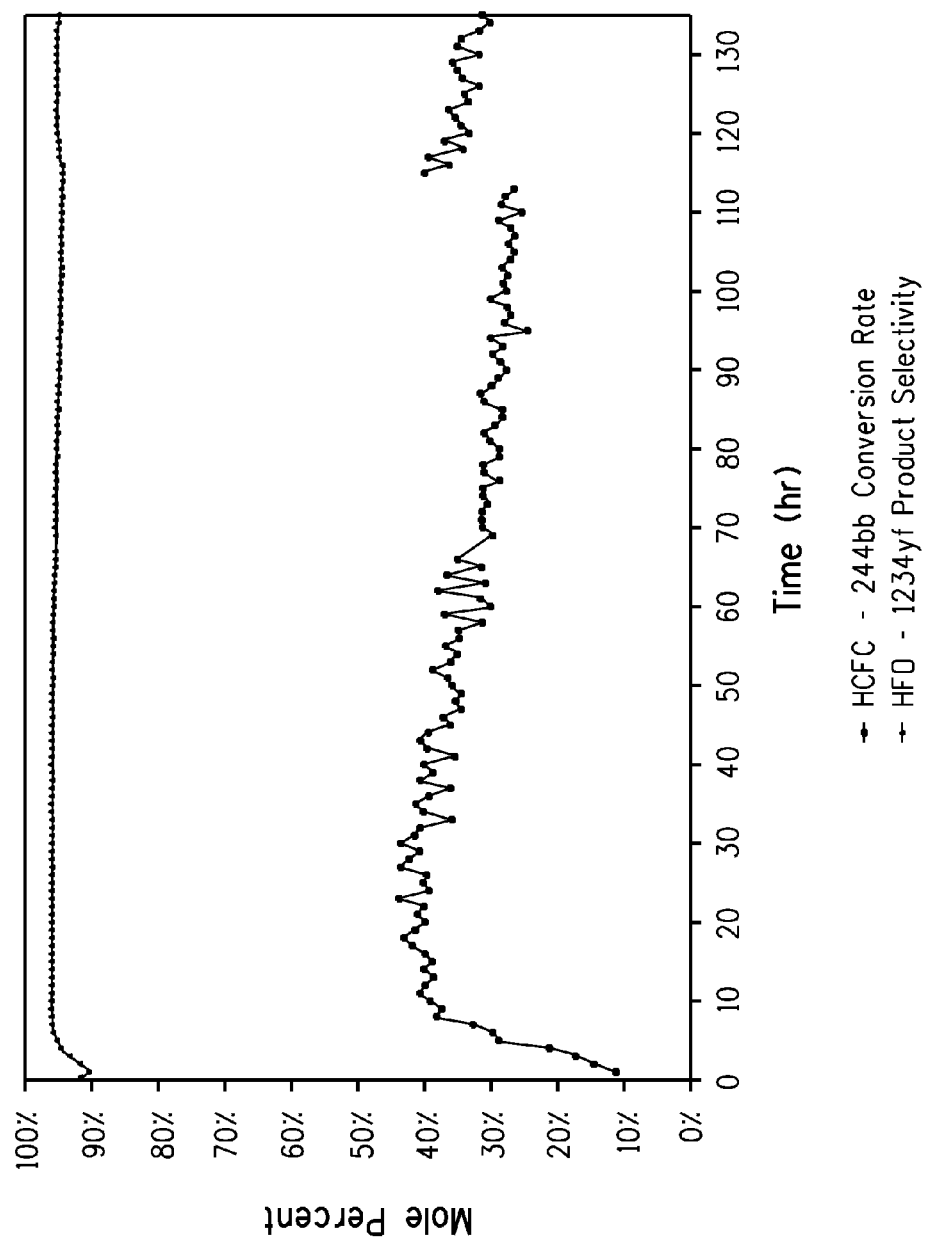
FIG. 1 is a graphical representation of the variations of the conversion rate of HCFC-244bb and the product selectivity to HFO-1234yf, described in Example 5, as the catalytic dehydrochlorination process continues, and after the catalyst is purged with nitrogen gas.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "dehydrochlorination", as used herein, means a process during which hydrogen and chlorine on adjacent carbons in a molecule are removed.

The term "hydrofluoroolefin", as used herein, means a molecule containing hydrogen, carbon, fluorine, and at least one carbon-carbon double bond. A hydrofluoroolefin in this disclosure may contain halogens other than fluorine such as chlorine, bromine and iodine. Exemplary hydrofluoroolefins in this disclosure include HFO-1234yf, HCFO-1233xf and HCFO-1224yd.

The term "alkyl", as used herein, either alone or in compound words such as "perfluorinated alkyl group", includes cyclic or acyclic and straight-chain or branched alkyl groups, such as, methyl, ethyl, n-propyl, i-propyl, or the different isomers thereof.

The term "perfluorinated alkyl group", as used herein, means an alkyl group wherein all hydrogens on carbon atoms have been substituted by fluorines. Examples of a perfluorinated alkyl group include —$CF_3$ and —$CF_2CF_3$.

The term "product selectivity to $R_fCF=CHX$", as used herein, means the molar percentage of $R_fCF=CHX$ obtained in the process compared to the total molar amounts of all products obtained.

The term "an elevated temperature", as used herein, means a temperature higher than the room temperature.

Disclosed is a dehydrochlorination process comprising contacting $R_fCFClCH_2X$ with a catalyst in a reaction zone to produce a product mixture comprising $R_fCF=CHX$, wherein said catalyst comprises MY supported on carbon, and wherein $R_f$ is a perfluorinated alkyl group, X=H, F, Cl, Br or I, M=K, Na or Cs, and Y=F, Cl or Br.

In some embodiments of this invention, $R_f$ is $-CF_3$ or $-CF_2CF_3$. In some embodiments of this invention, $R_fCFClCH_2X$ is $CF_3CFClCH_3$, and $R_fCF=CHX$ is $CF_3CF=CH_2$ (i.e., $R_f$ is $CF_3$ and X is H). In some embodiments of this invention, $R_fCFClCH_2X$ is $CF_3CFClCH_2Cl$, and $R_fCF=CHX$ is $CF_3CF=CHCl$ (i.e., $R_f$ is $CF_3$ and X is Cl).

Some hydrofluoroolefins of this disclosure, e.g., $CF_3CF=CHCl$, exist as different configurational isomers or stereoisomers. When the specific isomer is not designated, the present disclosure is intended to include all single configurational isomers, single stereoisomers, or any combination thereof. For instance, HCFO-1224yd ($CF_3CF=CHCl$) is meant to represent the E-isomer, Z-isomer, or any combination or mixture of both isomers in any ratio.

The starting materials for the dehydrochlorination processes in this disclosure, i.e., $R_fCFClCH_2X$, can be synthesized by methods known in the art. For example, HCFC-244bb ($CF_3CClFCH_3$) may be prepared by contacting HCFO-1233xf ($CF_3CCl=CH_2$) with HF in the presence of a catalyst having about 25 to about 99.9 mole percent antimony pentachloride and about 0.1 to about 75 mole percent of a metal of a Lewis acid as disclosed in the European Patent Publication EP2135855. For another example, HCFC-234ba ($CF_3CClFCH_2Cl$) may be prepared by the reaction of HFO-1234yf with $Cl_2$ or by the addition reaction of $CF_2=CFCl$ with $CH_2FCl$.

The dehydrochlorination process can be carried out in liquid phase or vapor phase using well-known chemical engineering practice, which includes continuous, semi-continuous or batch operations. The temperature in the reaction zone is typically from about 200° C. to about 500° C. In some embodiments of this invention, the temperature in the reaction zone is from about 320° C. to about 380° C. The dehydrochlorination process can be conducted at superatmospheric, atmospheric, or subatmospheric pressures. The contact time of the starting material $R_fCFClCH_2X$ with the catalyst can be largely varied. Typically, the contact time is from about 10 seconds to about 150 seconds. In some embodiments of this invention, the contact time is from about 40 seconds to about 100 seconds.

The contacting step of this invention may be carried out by methods known in the art. In some embodiments of this invention, starting material $R_fCFClCH_2X$, optionally with an inert gas, is fed to a reactor containing the catalyst. In some embodiments of this invention, starting material $R_fCFClCH_2X$, optionally with an inert gas, is passed through the catalyst bed in a reactor. In some embodiments of this invention, starting material $R_fCFClCH_2X$, optionally together with an inert gas, may be mixed with the catalyst in a reactor with stir or agitation.

The dehydrochlorination process may be conducted in the presence of an inert gas such as He, Ar, or $N_2$. In some embodiments of this invention, the inert gas is co-fed into the reactor with the starting material.

In accordance with this invention, catalysts suitable for dehydrochlorination are provided. Said catalysts comprise carbon supported alkali metal halide salt represented by the formula MY, wherein M=K, Na or Cs, and Y=F, Cl or Br. In some embodiments of this invention, MY is KF. In some embodiments of this invention, MY is KCl. The alkali metal halide salt can be deposited on the carbon support using deposit techniques well known in the art. For example, alkali metal halide salt can be dissolved in deionized water and then mixed with freshly dried acid washed activated carbon. The mixture can be gently stirred until the solution of the alkali metal halide salt is completely absorbed by the activated carbon. Finally, the loaded activated carbon is dried at an elevated temperature and stored in a sealed container for use as a catalyst. In some embodiments of this invention, the catalyst contains from about 5 wt % (weight percent) to about 40 wt % alkali metal halide salt based on the total amount of alkali metal halide salt and carbon. In some embodiments of this invention, the catalyst contains from about 10 wt % to about 30 wt % alkali metal halide salt based on the total amount of alkali metal halide salt and carbon.

Carbon used in the embodiments of this invention may come from any of the following sources: wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™ Columbia LCK™, Calgon™ PCB, Calgon™ BPL, Westvaco™, Norit™, Takeda™ and Barnaby Cheny NB™.

The carbon also includes three dimensional matrix porous carbonaceous materials. Examples are those described in U.S. Pat. No. 4,978,649. In one embodiment of the invention, carbon includes three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Carbon includes unwashed and acid-washed carbons. In some embodiments of this invention, suitable catalysts may be prepared by treating the carbon used as catalyst support with acids such as $HNO_3$, HCl, HF, $H_2SO_4$, $HClO_4$, $CH_3COOH$, and combinations thereof. Acid treatment is typically sufficient to provide carbon that contains less than 1000 ppm of ash. Some suitable acid treatments of carbon are described in U.S. Pat. No. 5,136,113. In some embodiments of this invention, an activated carbon is dried at an elevated temperature and then is soaked for 8 to 24 hours with occasional stirring in 1 to 12 weight percent of $HNO_3$. The soaking process can be conducted at temperatures ranging from room temperature to 80° C. The activated carbon is then filtered and washed with deionized water until the washings have a pH greater than 4.0 or until the pH of the washings does not change. Finally, the activated carbon is dried at an elevated temperature.

In some embodiments of this invention, carbon is an activated carbon. In some embodiments of this invention, carbon is an acid washed activated carbon. The carbon can be in the form of powder, granules, or pellets, et al.

The effluent from the reaction zone typically includes residual starting materials $R_fCFClCH_2X$, desired hydrofluoroolefin product $R_fCF=CHX$ and some byproducts. The desired product $R_fCF=CHX$ may be recovered from the product mixture by conventional methods. In some embodiments of this invention, product $R_fCF=CHX$ may be purified or recovered by distillation.

It was found through experiments that the catalytic dehydrochlorination processes of this disclosure produced desired products with high selectivity. In some embodiments of this invention, the product selectivity to $R_fCF=CHX$ is at least 90 mole %. In some embodiments of this invention, the product selectivity to $R_fCF=CHX$ is at least 96 mole %.

In some embodiments of this invention, the catalyst's activity may decrease as the dehydrochlorination process continues. It was found through experiments that the catalyst can be regenerated or the catalyst's activity can be recovered by purging with inert gases. Accordingly, in some embodiments of this invention, the dehydrochlorination process further comprises purging the catalyst with an inert gas. The inert gas can be selected from the group consisting of He, Ar, $N_2$, and any combinations thereof. In some embodiments of this invention, the dehydrochlorination process further comprises purging the catalyst with $N_2$.

The purging process can be done by passing an inert gas through the catalyst at an elevated temperature. In some embodiments of this invention, the temperature is from about 200° C. to about 500° C. In some embodiments of this invention, the temperature is from about 320° C. to about 380° C. In some embodiments of this invention, the temperature in the purging process is about the same as in the dehydrochlorination stage. In some embodiments of this invention, the flow rate of the inert gas during the purging processes is from about 5 times to about 50 times of the $R_fCFClCH_2X$ flow rate in the dehydrochlorination stage. In some embodiments of this invention, the flow rate of the inert gas during the purging processes is from about 10 times to about 30 times of the $R_fCFClCH_2X$ flow rate in the dehydrochlorination stage. The purge time varies depending on the recovery rate of the catalyst activity. Typically, the purge time is from about 1 hour to about 12 hours.

Typically, during the purging process the starting material $R_fCFClCH_2X$ is stopped being fed into the reactor. In some embodiments of this invention, after detecting a significant drop of the catalyst activity, the $R_fCFClCH_2X$ inflow to the reactor is discontinued and replaced by an inert gas with an inflow rate from about 5 times to about 50 times of the previous $R_fCFClCH_2X$ inflow rate, while the temperature of the reactor remains the same. At the end of the purge process, the inert gas for the purge is discontinued and the $R_fCFClCH_2X$ inflow is resumed.

The reactors, distillation columns, and their associated feed lines, effluent lines, and associated units used in applying the processes of embodiments of this invention may be constructed of materials resistant to corrosion. Typical materials of construction include Teflon™ and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Preparation of $HNO_3$ Washed Carbon

An activated carbon with surface area in the range of from about 1200 to about 1500 $m^2/g$ was soaked in 1 wt % $HNO_3$ aqueous solution at room temperature for 12 hours before being fully washed with deionized water and dried at 120° C. for 12 hours. Some of the $HNO_3$ washed activated carbons prepared above were loaded with KF and used in Example 1, and some were loaded with KCl and used in Examples 2 and 3.

Preparation of $HNO_3$ Washed Takeda™ Carbon

Takeda™ activated carbon with surface area ranging from about 1000 $m^2/g$ to about 1200 $m^2/g$ was soaked in 1 wt % $HNO_3$ aqueous solution at room temperature for 12 hours before being fully washed with deionized water and dried at 120° C. for 12 hours. The $HNO_3$ washed Takeda™ carbon was then loaded with KCl and used in Examples 4 and 5.

Preparation of $HNO_3$ Washed Takeda™ Carbon

Takeda™ activated carbon with surface area ranging from about 1000 $m^2/g$ to about 1200 $m^2/g$ was soaked in 8 wt % $HNO_3$ aqueous solution at 60° C. for 12 hours before being fully washed with deionized water and dried at 120° C. for 12 hours. The Takeda™ carbon as prepared above was then loaded with KCl and used in Example 7.

Example 1

Example 1 demonstrates that contacting HCFC-244bb with KF supported on acid washed activated carbon generates HFO-1234yf.

10 cc (cubic centimeter) of catalyst granules of 20 wt % KF/acid washed activated carbon were loaded into a 0.43 inch I. D. Monel™ reactor tube to form a catalyst bed. A gaseous mixture of 98.8 mole % of HCFC-244bb and 1.2 mole % of HCFO-1233xf ($CF_3CCl=CH_2$) was passed through the catalyst bed at a rate of 1.1 g/hr together with 4.3 ml/min $N_2$. The back pressure was about atmospheric pressure. The effluent from the reactor tube was analyzed by GC and GC-MS. The conversion rate of the starting material HCFC-244bb and the product selectivity to HFO-1234yf were listed in the Table 1 below which shows good product selectivity to HFO-1234yf over a wide range of temperatures.

TABLE 1

| Temp. ° C. | Conversion Mole % HCFC-244bb | Selectivity Mole % HFO-1234yf |
|---|---|---|
| 225 | 14.86 | 91.89 |
| 230 | 14.36 | 91.16 |
| 279. | 28.03 | 94.19 |
| 275 | 15.52 | 92.15 |
| 327 | 23.49 | 94.63 |
| 329 | 7.63 | 87.86 |
| 377 | 41.09 | 96.52 |
| 377 | 54.62 | 97.80 |
| 375 | 57.82 | 97.89 |
| 374 | 65.63 | 98.22 |
| 376 | 72.83 | 98.19 |
| 390 | 82.75 | 96.28 |
| 403 | 89.60 | 98.04 |
| 399 | 88.39 | 97.45 |
| 427 | 96.33 | 96.43 |
| 424 | 96.03 | 95.32 |

The stability of the catalyst was tested under the same process conditions as described above at about 385° C. At the end of every hour, the effluent from the reactor tube was analyzed by GC and GC-MS. The results were listed in the Table 2 below.

TABLE 2

| Time hr | Conversion Mole % HCFC-244bb | Selectivity Mole % HFO-1234yf |
|---|---|---|
| 1 | 82.81 | 95.90 |
| 2 | 77.78 | 96.13 |
| 3 | 76.91 | 96.36 |
| 4 | 72.82 | 96.31 |
| 5 | 73.07 | 96.10 |
| 6 | 74.47 | 96.06 |
| 7 | 70.06 | 95.72 |
| 8 | 72.07 | 96.22 |
| 9 | 70.70 | 96.01 |
| 10 | 69.04 | 96.45 |
| 11 | 70.57 | 96.27 |

Example 2

Example 2 demonstrates that contacting HCFC-244bb with KCl supported on acid washed activated carbon generates HFO-1234yf.

10 cc of catalyst granules of 25 wt % KCl/acid washed activated carbon were loaded into a 0.43 inch I. D. Monel™ reactor tube to form a catalyst bed. A gaseous mixture of 99.7 mole % of HCFC-244bb and 0.3 mole % of HCFO-1233xf was passed through the catalyst bed at a rate of 1.1 g/hr together with 4.3 ml/min $N_2$. The back pressure was about atmospheric pressure. The effluent from the reactor tube was analyzed by GC and GC-MS. The conversion rate of the starting material HCFC-244bb and the product selectivity to HFO-1234yf were listed in the Table 3 below which shows good product selectivity to HFO-1234yf over a wide range of temperatures.

TABLE 3

| Temp. ° C. | Conversion Mole % HCFC-244bb | Selectivity Mole % HFO-1234yf |
|---|---|---|
| 278 | 4.37 | 96.13 |
| 276 | 2.94 | 93.90 |
| 326 | 8.42 | 97.81 |
| 322 | 5.08 | 96.60 |
| 377 | 49.08 | 98.97 |
| 375 | 56.48 | 99.14 |
| 386 | 89.99 | 97.80 |
| 385 | 90.78 | 97.57 |
| 396 | 93.28 | 97.14 |
| 403 | 95.23 | 96.89 |
| 427 | 96.80 | 98.27 |
| 423 | 98.01 | 96.80 |

The stability of the catalyst was tested under the same process conditions as described above at about 385° C. At the end of every hour, the effluent from the reactor tube was analyzed by GC and GC-MS. The results were listed in the Table 4 below.

TABLE 4

| Time hr | Conversion Mole % HCFC-244bb | Selectivity Mole % HFO-1234yf |
|---|---|---|
| 1 | 89.99 | 97.80 |
| 2 | 90.78 | 97.57 |
| 3 | 90.80 | 97.83 |
| 4 | 91.40 | 97.63 |
| 5 | 91.31 | 97.61 |
| 6 | 91.27 | 97.82 |
| 7 | 89.45 | 97.61 |

TABLE 4-continued

| Time hr | Conversion Mole % HCFC-244bb | Selectivity Mole % HFO-1234yf |
|---|---|---|
| 8 | 89.65 | 97.83 |
| 9 | 86.91 | 97.83 |
| 10 | 88.70 | 97.76 |
| 11 | 89.65 | 97.83 |
| 12 | 86.91 | 97.83 |
| 13 | 88.70 | 97.76 |

Example 3

Example 3 demonstrates that the carbon supported KCl catalyst works well under high back pressure.

All the process conditions were the same as in Example 2 except that the back pressure here was 45 psig (pounds per square inch gauge). The analytical results of the effluent from the reactor tube were list in Table 5 below.

TABLE 5

| Temp. ° C. | Conversion Mole % HCFC-244bb | Selectivity Mole % HFO-1234yf |
|---|---|---|
| 353 | 43.72 | 98.88 |
| 351 | 27.41 | 98.50 |
| 375 | 52.28 | 98.14 |
| 374 | 50.17 | 98.17 |
| 401 | 77.89 | 96.75 |
| 425 | 89.94 | 95.05 |

Example 4

Example 4 demonstrates that contacting HCFC-234ba with KCl supported on acid washed Takeda™ carbon generates HCFO-1224yd.

10 cc of catalyst granules of 25 wt % KCl/acid washed Takeda™ carbon were loaded into a 0.43 inch I. D. Monel™ reactor tube to form a catalyst bed. A gaseous mixture of 96 mole % of HCFC-234ba and 4 mole % of HFO-1234yf was passed through the catalyst bed at a rate of 1.1 g/hr together with 4.3 ml/min $N_2$. The back pressure was about atmospheric pressure. The effluent from the reactor tube was analyzed by GC and GC-MS. The conversion rate of the starting material HCFC-234ba and the product selectivity to HCFO-1224yd were listed in the Table 6 below which shows high conversion rate of HCFC-234ba and good product selectivity to HCFO-1224yd over a wide range of temperatures.

TABLE 6

| Temp. ° C. | Conversion Mole % HCFC-234ba | Selectivity Mole % trans-HCFC-1224yd | Selectivity Mole % cis-HCFC-1224yd |
|---|---|---|---|
| 241 | 70.73% | 90.96% | 7.05% |
| 247 | 74.04% | 91.03% | 6.81% |
| 275 | 99.90% | 89.29% | 5.98% |
| 275 | 99.88% | 88.32% | 6.23% |
| 295 | 100.00% | 93.57% | 5.00% |
| 302 | 100.00% | 93.47% | 5.04% |
| 318 | 100.00% | 91.64% | 5.36% |
| 325 | 100.00% | 92.13% | 5.53% |
| 350 | 100.00% | 91.67% | 6.20% |
| 350 | 100.00% | 90.52% | 6.13% |
| 373 | 100.00% | 84.62% | 6.40% |

Example 5

Example 5 demonstrates that N$_2$ purge can regenerate the carbon supported KCl catalyst to recover the conversion rate of the starting material HCFC-244bb.

10 cc of catalyst granules of 25 wt % KCl/acid washed Takeda™ carbon were loaded into a 0.43 inch I. D. Monel™ reactor tube to form a catalyst bed. A gaseous mixture of 99.4 mole % of HCFC-244bb and 0.6 mole % of HCFO-1233xf was passed through the catalyst bed at a rate of 1.1 g/hr together with 4.3 ml/min N$_2$. The back pressure was about atmospheric pressure. The effluent from the reactor tube was analyzed by GC and GC-MS.

The stability of the catalyst was tested at about 350° C. It was found that after 113 run hours, the conversion rate of HCFC-244bb dropped from about 40 mole % to about 25 mole %. The HCFC-244bb/HCFO-1233xf/N$_2$ inflow passing through the catalyst bed was discontinued, and the catalyst was then purged with 150 sccm (Standard Cubic Centimeters per Minute) of N$_2$ for 3 hours at about 350° C. After purge, the HCFC-244bb/HCFO-1233xf/N$_2$ inflow was resumed and it was found that the conversion rate bounced back to about 38 mole %. The product selectivity to HFO-1234yf was consistently at the level of about 95 mole % during the totally 130 run hours test. The results are shown in FIG. 1.

Example 6

Example 6 demonstrates that contacting HCFC-244bb with KCl supported on unwashed activated carbon generates HFO-1234yf.

10 cc of catalyst granules (6-10 mesh) of 25 wt % KCl/unwashed Calgon Carbon COCO Plus (an activated carbon with surface area ranging from about 900 m$^2$/g to about 1200 m$^2$/g) were loaded into a 0.43 inch I. D. Monel™ reactor tube to form a catalyst bed. A gaseous mixture of 99.7 mole % of HCFC-244bb and 0.3 mole % of HCFO-1233xf was passed through the catalyst bed at a rate of 1.1 g/hr together with 4.3 ml/min N$_2$. The back pressure was about atmospheric pressure. The effluent from the reactor tube was analyzed by GC and GC-MS. The conversion rate of the starting material HCFC-244bb and the product selectivity to HFO-1234yf, along with the run time, were listed in the Table 7 below.

TABLE 7

| Time hr | Temp. ° C. | Conversion Mole % HCFC-244bb | Selectivity Mole % HFO-1234yf |
|---|---|---|---|
| 1 | 375 | 36.91% | 90.52% |
| 2 | 373 | 54.45% | 96.77% |
| 3 | 402 | 82.28% | 98.43% |
| 4 | 386 | 73.00% | 98.22% |
| 5 | 384 | 71.59% | 97.68% |
| 6 | 386 | 72.82% | 96.79% |
| 7 | 386 | 72.11% | 97.09% |
| 8 | 387 | 73.77% | 96.84% |
| 9 | 385 | 69.60% | 96.85% |
| 10 | 387 | 70.04% | 96.22% |
| 11 | 423 | 84.52% | 85.46% |
| 12 | 424 | 79.81% | 84.46% |
| 13 | 394 | 58.46% | 86.95% |
| 14 | 401 | 61.35% | 86.95% |
| 15 | 401 | 57.46% | 86.40% |
| 16 | 398 | 53.38% | 87.35% |
| 17 | 401 | 53.58% | 86.78% |
| 18 | 401 | 52.17% | 86.61% |
| 19 | 394 | 41.79% | 88.88% |
| 20 | 402 | 48.86% | 87.50% |
| 21 | 401 | 42.71% | 88.54% |
| 22 | 398 | 39.89% | 89.01% |

Example 7

Example 7 demonstrates that contacting HCFC-244bb with 5 wt % KCl/acid washed Takeda™ carbon generates HFO-1234yf.

Figure 2:
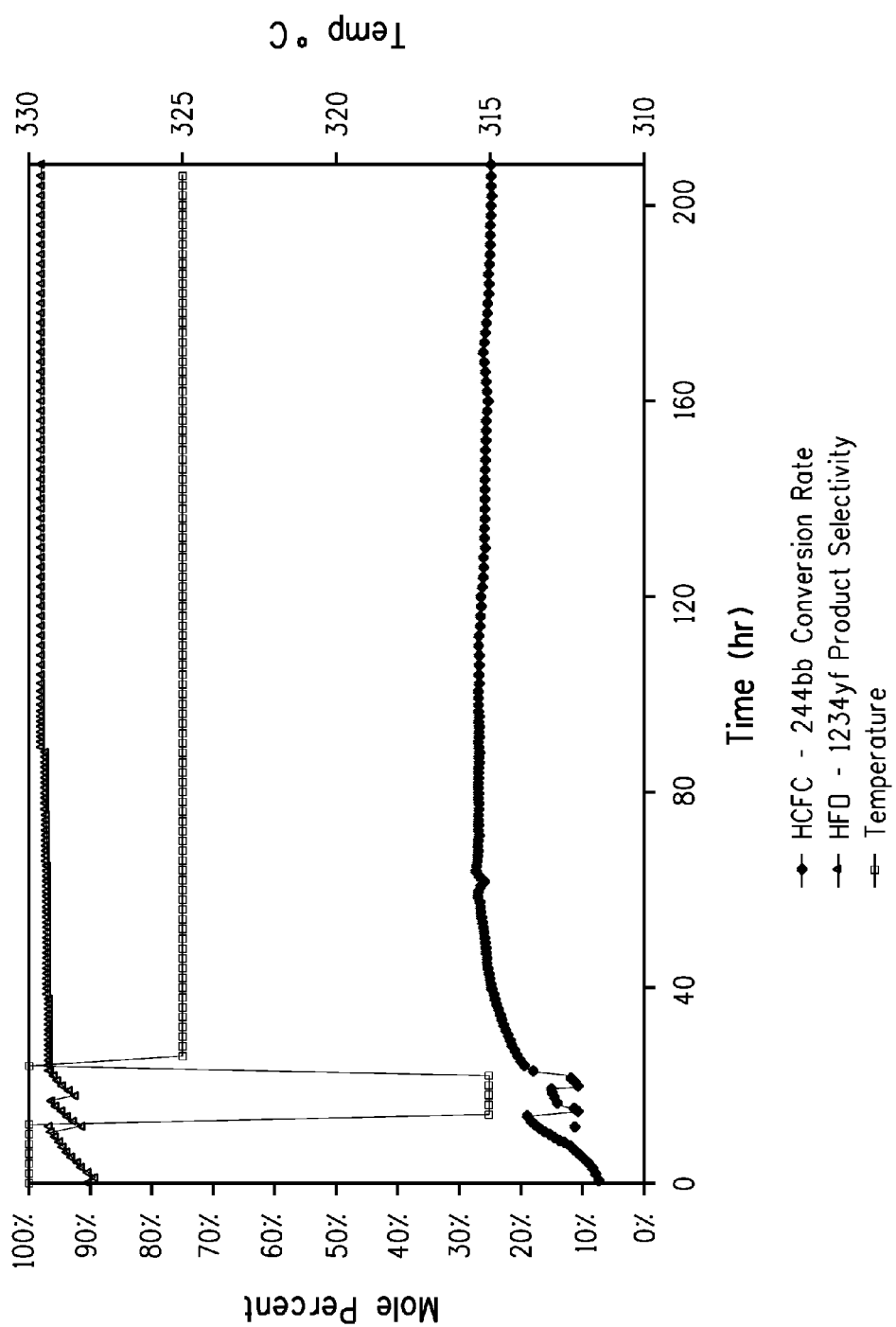
FIG. 2 is a graphical representation of the analytical results of the catalytic dehydrochlorination processes described in Example 7.

10 cc of catalyst granules (6-10 mesh) of 5 wt % KCl/acid washed Takeda™ carbon were loaded into a 0.43 inch I. D. Monel™ reactor tube to form a catalyst bed. A gaseous mixture of 99.7 mole % of HCFC-244bb and 0.3 mole % of HCFO-1233xf was passed through the catalyst bed at a rate of 7.3 sccm. The back pressure was about atmospheric pressure. The effluent from the reactor tube was analyzed by GC and GC-MS. The conversion rate of the starting material HCFC-244bb and the product selectivity to HFO-1234yf, along with the temperature and the run time, were shown in FIG. 2. The catalyst showed good selectivity (above 90 mole %) to HFO-1234yf and good stability at 325° C.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A dehydrochlorination process comprising contacting R$_f$CFClCH$_2$X with a catalyst in a reaction zone to produce a product mixture comprising R$_f$CF=CHX, wherein said catalyst comprises an alkali metal halide salt represented by the formula MY which is supported on carbon, and wherein R$_f$ is a perfluorinated alkyl group, X=H, F, Cl, Br or I, M=K, Na or Cs, and Y=F, Cl or Br, and wherein the catalyst contains from about 5 wt % to about 40 wt % of alkali metal halide salt based on the total amount of alkali metal halide salt and carbon.

2. The dehydrochlorination process of claim 1 wherein the carbon is an activated carbon.

3. The dehydrochlorination process of claim 2 wherein the carbon is an acid washed activated carbon.

4. The dehydrochlorination process of claim 1 wherein M is K and Y is F or Cl.

5. The dehydrochlorination process of claim 1 wherein the temperature in the reaction zone is from about 200° C. to about 500° C.

6. The dehydrochlorination process of claim 5 wherein the temperature in the reaction zone is from about 320° C. to about 380° C.

7. The dehydrochlorination process of claim 1 wherein the product selectivity to $R_fCF=CHX$ is at least 90 mole %.

8. The dehydrochlorination process of claim 1 wherein the product selectivity to $R_fCF=CHX$ is at least 96 mole %.

9. The dehydrochlorination process of claim 1 wherein $R_fCFClCH_2X$ is $CF_3CFClCH_2Cl$, and $R_fCF=CHX$ is $CF_3CF=CHCl$.

10. The dehydrochlorination process of claim 1 wherein $R_fCFClCH_2X$ is $CF_3CFClCH_3$, and $R_fCF=CHX$ is $CF_3CF=CH_2$.

11. The dehydrochlorination process of claim 1, further comprising regenerating said catalyst by purging the catalyst with an inert gas.

12. The dehydrochlorination process of claim 11 wherein the inert gas is $N_2$.

13. The dehydrochlorination process according to claim 1 where in the catalyst contains from about 10 wt % to about 30 wt % alkali metal halide salt based on the total amount of alkali metal halide salt and carbon.

\* \* \* \* \*